(12) United States Patent
Duyck et al.

(10) Patent No.: US 6,916,767 B2
(45) Date of Patent: Jul. 12, 2005

(54) ANTIOXIDANT AMINES BASED ON N-(4ANILIOPHENYL) AMIDES ANTIOXIDANT AMINES BASED ON N-(4-ANILINOPHENYL) AMIDES

(75) Inventors: Karl J. Duyck, Waterbury, CT (US); Theodore E. Nalesnik, Hopewell Junction, NY (US)

(73) Assignee: Uniroyal Chemical Company, Inc., Middlebury, CT (US)

(*) Notice: Subject to any disclaimer, the term of this patent is extended or adjusted under 35 U.S.C. 154(b) by 568 days.

(21) Appl. No.: 10/168,405

(22) PCT Filed: Dec. 5, 2000

(86) PCT No.: PCT/US00/32951

§ 371 (c)(1),
(2), (4) Date: Jun. 19, 2002

(87) PCT Pub. No.: WO01/49761

PCT Pub. Date: Jul. 12, 2001

(65) Prior Publication Data

US 2003/0030033 A1 Feb. 13, 2003

Related U.S. Application Data

(60) Provisional application No. 60/173,715, filed on Dec. 30, 1999.

(51) Int. Cl.[7] .................... C08F 255/04; C10M 133/16; C10M 149/00; C10M 159/12
(52) U.S. Cl. ..................... 508/221; 508/248; 508/251; 508/256; 508/261; 508/376; 508/454; 508/551; 508/555; 544/35; 544/38; 544/102; 544/347; 546/102; 564/193; 564/194; 564/196; 525/326.1; 525/375; 525/379
(58) Field of Search ........................... 544/35, 38, 102, 544/347; 508/261, 251, 256, 248, 551, 555

(56) References Cited

U.S. PATENT DOCUMENTS

| | | | |
|---|---|---|---|
| 3,452,056 A | 6/1969 | Sundholm ................... 260/390 |
| 3,505,225 A | 4/1970 | Wheeler ..................... 252/33.6 |
| 3,522,180 A | 7/1970 | Sweeney et al. .............. 252/59 |
| 4,026,809 A | 5/1977 | Lachowicz et al. ........ 252/51.5 |
| 4,089,794 A | 5/1978 | Engel et al. ............... 252/51.5 |
| 4,096,319 A | 6/1978 | Willette et al. ............... 526/16 |
| 4,137,185 A | 1/1979 | Gardiner et al. ............. 252/33 |
| 4,144,181 A | 3/1979 | Elliott et al. .................. 252/33 |
| 4,146,489 A | 3/1979 | Stambaugh et al. .......... 252/50 |
| 4,234,435 A | 11/1980 | Meinhardt et al. ......... 252/51.5 |
| 4,320,019 A | 3/1982 | Hayashi ..................... 252/51.5 |
| 4,340,689 A | 7/1982 | Joffrion ..................... 525/263 |
| 4,357,250 A | 11/1982 | Hayashi ..................... 252/51.5 |
| 4,382,007 A | 5/1983 | Chafetz et al. ............. 252/51.5 |
| 4,668,834 A | 5/1987 | Rim et al. ..................... 585/12 |
| 4,670,515 A | 6/1987 | Olivier ....................... 525/285 |
| 4,797,511 A | 1/1989 | Capolupo et al. ........... 174/110 |
| 4,837,259 A | 6/1989 | Chucta ....................... 524/258 |
| 4,863,623 A | 9/1989 | Nalesnik ...................... 252/50 |
| 4,904,403 A | 2/1990 | Karol ......................... 252/47.5 |
| 4,948,842 A | 8/1990 | Olivier ....................... 525/286 |
| 4,990,274 A | 2/1991 | Nalesnik ...................... 252/52 |
| 5,021,177 A | 6/1991 | Kapuscinski et al. ...... 252/51.5 |
| 5,047,530 A | 9/1991 | Wheeler et al. ............. 544/197 |
| 5,075,383 A | 12/1991 | Migdal et al. ............. 525/293 |
| 5,094,766 A | 3/1992 | Kapuscinski et al. ...... 252/51.5 |
| 5,120,844 A | 6/1992 | Wheeler et al. ............. 544/209 |
| 5,162,086 A | 11/1992 | Migdal et al. ............. 252/47.5 |
| 5,188,745 A | 2/1993 | Migdal et al. ................ 252/47 |

(Continued)

FOREIGN PATENT DOCUMENTS

EP 0922752 A2 6/1999

OTHER PUBLICATIONS

Kuczkowski, J.A. et al., Rubber Chemistry and Technology, 57:621 (1984).

Mirshra, M. K. et al., Polym. Sci. (Symp. Proc. Polym. '91), vol. 2, 694–699.

*Primary Examiner*—Ellen M McAvoy
(74) *Attorney, Agent, or Firm*—Michael P. Dilworth

(57) ABSTRACT

A composition of matter is disclosed wherein the composition comprises an N-aromatic substituted acid amide compound selected from the group consisting of compounds of formula (I) wherein A and B are independently selected alkylene groups; $R_1$ is selected from the group consisting of hydrogen, alkyl, alkylether, or ester; $R_2$ is hydrogen if $R_1$ is hydrogen; $R_2$ is an alkyl primary amine if $R_1$ is alkyl, alkylether, or ester; $R_3$ and $R_4$ are independently selected from the group consisting of hydrogen and alkyl; $R_5$ is a sterically hindered phenolic group of formula (II) or formula (III) wherein X is $CH_2$, S, NH, or O; and m, n, and p are independently selected integers equal to 0 or 1. These compositions may be used as such or they may be bound to a polymer backbone via a linking moiety. In either case, they are useful as antioxidants, particularly in lubricating oil compositions

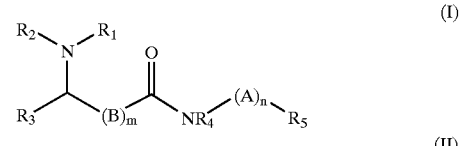

(I)

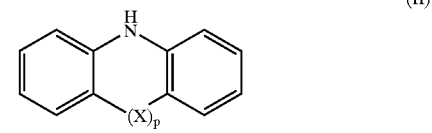

(II)

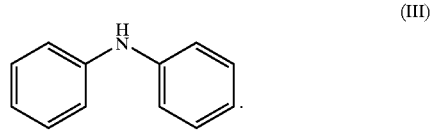

(III)

16 Claims, No Drawings

U.S. PATENT DOCUMENTS

| | | | |
|---|---|---|---|
| 5,200,102 A | | 4/1993 | Mishra et al. .............. 252/47.5 |
| 5,439,607 A | * | 8/1995 | Patil ........................... 508/239 |
| 5,474,694 A | | 12/1995 | Shirodkar et al. ......... 252/51.5 |
| 5,498,809 A | | 3/1996 | Emert et al. ................... 585/13 |
| 5,556,923 A | | 9/1996 | Caines et al. ............... 525/285 |
| 5,698,500 A | | 12/1997 | Baranski et al. ............ 508/273 |
| 5,747,433 A | | 5/1998 | Luciani et al. ............... 508/479 |
| 5,834,544 A | | 11/1998 | Lin et al. ..................... 524/217 |
| 6,107,257 A | | 8/2000 | Valcho et al. ................ 508/221 |
| 6,107,258 A | | 8/2000 | Esche, Jr. et al. ........... 508/231 |
| 6,117,825 A | | 9/2000 | Liu et al. ..................... 508/291 |
| 6,734,324 B2 | * | 5/2004 | Glufke et al. ................ 564/200 |

* cited by examiner

ANTIOXIDANT AMINES BASED ON N-(4ANILIOPHENYL) AMIDES ANTIOXIDANT AMINES BASED ON N-(4-ANILINOPHENYL) AMIDES

This application claims the benefit of provisional application Ser. No. 60/173,715 filed Dec. 30, 1999.

BACKGROUND OF THE INVENTION

1. Field of the Invention

This invention relates to the protection of organic materials, such as rubber, plastic, lubricating oils, petroleum fuels, waxes, and organic liquids, from oxidation by the use of antioxidants that are N-aromatic substituted acid amide compounds.

In a preferred embodiment, the present invention is directed to lubricants, especially lubricating oils. More particularly, the invention relates to a class of dispersant additives having antioxidant and viscosity index improving credit that are preferably derived from an ethylene-propylene diene modified terpolymer (EPDM) or an ethylene-propylene copolymer and an N-aromatic substituted acid amide compound.

2. Description of Related Art

Organic materials such as rubber, plastic, lubricating oils, petroleum fuels, waxes, and organic liquids are well known to need protection from oxidation.

Currently, many of these organic materials are being exposed to higher operating temperatures and mechanical shear. New stabilizers that can protect organic materials from premature oxidation and degradation under these advanced operating conditions are being sought.

Further, in developing lubricating oils, there have been many attempts to provide additives that provide a lubricating oil with dispersancy of sludge and soot as well as high temperature deposit control. In addition, the formulation of an oil to meet high and low temperature viscosity requirements is critical and, in most cases, a viscosity index improver is employed to achieve this goal. Most multifunctional additives of the prior art provide one or two of these features.

It is well-known that internal combustion engines operate under a wide range of temperatures, including low temperature stop-and-go driving service, as well as high-temperature conditions produced by continuous high speed driving. Stop-and-go driving, particularly under cold, damp weather conditions, leads to the formation of sludge in the crankcase and in the oil passages of a gasoline or a diesel engine. This sludge seriously limits the ability of the crankcase engine oil to lubricate the engine effectively. In addition, the sludge, with its entrapped water, tends to contribute to rust formation in the engine. These problems can be aggravated by engine manufacturers' lubrication service recommendations, which typically specify extended oil drain intervals.

Additives that protect engines against sludge formation generally contain nitrogen. These additives are also known as dispersants and/or detergents in the formulation of crankcase lubricating oil compositions. The preparation of many of the known dispersant/detergent compounds is based on the reaction of an alkenylsuccinic acid or anhydride with an amine or polyamine to produce an alkenyl succinimide or an alkenylsuccinamic acid or anhydride as an intermediate. This is advantageous since these products, if not completely reacted with amine or polyamine, can cause rust in an engine.

It is common practice to chlorinate the alkenyl group either before or after reaction with the acid anhydride, but prior to reaction with the amine or polyamine, in order to produce a reaction product in which a portion of the amine or polyamine is attached directly to the alkenyl moiety. The thrust of many of these processes is to produce a product having a relatively high level of nitrogen in order to provide improved dispersancy. However, chlorine is an environmentally undesirable by-product of such processes, and it would therefore be advantageous to achieve relatively high levels of nitrogen without the use of chlorine.

Ethylene-propylene copolymers and ethylene-alpha olefin non-conjugated diene terpolymers that have been grafted and derivatized to provide valuable properties in lubricating oil compositions are well known.

Aralkyl-substituted diarylamines, such as 4,4'-bis($\alpha,\alpha$-dimethylbenzyl)diphenylamine (NAUGARD 445, Uniroyal Chemical), and their use as antioxidants for a variety of polymeric materials are known from U.S. Pat. Nos. 3,452,056 and 3,505,225.

Additionally, aromatic amines have also been used as stabilizers of organic materials, especially for use in plastic, rubber, and oils. For example, U.S. Pat. No. 3,505,225 describes aromatic amine antioxidants based on $\alpha$-methylstyryl-substituted diphenylamines.

U.S. Pat. No. 3,522,180 discloses a method for the preparation of an ethylene-propylene copolymer substrate effective as a viscosity index improver for lubricating oils.

U.S. Pat. No. 4,026,809 discloses graft copolymers of a methacrylate ester and an ethylene-propylene-alkylidene norbornene terpolymer as a viscosity index improver for lubricating oils.

U.S. Pat. No. 4,089,794 discloses ethylene copolymers derived from ethylene and one or more $C_3$ to $C_{28}$ alpha olefins solution-grafted with an ethylenically-unsaturated carboxylic acid material followed by a reaction with a polyfunctional material, such as a polyamine, a polyol, or a hydroxylamine that is reactive with the carboxyl groups of the acid.

U.S. Pat. No. 4,096,319 discloses polymers containing anti-oxidant functionality that are said to be useful as viscosity index (VI) improvers for high temperature service. The anti-oxidant moiety is said to prevent extensive oxidative decomposition of the polymer making the polymers particularly useful with lubricating oils used in diesel engines. A method of preparing the antioxidant-containing VI improver polymer by esterifying a carboxylic acid-containing polymer with an N-methyl hydroxyethyl amide-containing antioxidant is also disclosed.

U.S. Pat. Nos. 4,137,185 and 4,144,181 disclose an oil-soluble, derivatized ethylene copolymer derived from about 2 to 98 wt. percent ethylene, and one or more $C_3$ to $C_{28}$ alpha-olefins, e.g., propylene. These compounds are preferably solution-grafted under an inert atmosphere and at elevated temperatures in the presence of a high-temperature, decomposable free-radical initiator with an ethylenically-unsaturated dicarboxylic acid material. Thereafter, the graft copolymer is reacted with a polyamine having at least two primary amine groups, e.g., an alkylene polyamine such as diethylene triamine, to form carboxyl-grafted polymeric imide, usually maleimide, derivatives. The derivatives are reacted with an anhydride of a $C_1$ to $C_{30}$ hydrocarbyl substituted acid, preferably acetic anhydride, to yield an oil-soluble, stable amide derivative of the polyamine that exhibits minimal viscosity change over an extended period of time. Useful number average molecular weights ($M_n$) of the copolymers range from about 700 to 500,000. If the molecular weight is in the range of 10,000 to 500,000, then these copolymers are also useful as multifunctional viscosity index improvers.

U.S. Pat. No. 4,146,489 discloses graft copolymers wherein the backbone polymer is a rubbery, oil-soluble ethylene-propylene copolymer or ethylene-propylene diene modified terpolymer and the graft monomer is a C-vinylpyridine or N-vinylpyrrolidone that imparts dispersant properties to hydrocarbon fuels and combined viscosity index improvement and dispersant properties to lubricating oils for internal combustion engines. The graft copolymers are prepared by intimate admixture of the backbone polymer, monomer to be grafted, and a free radical initiator at a temperature below initiation temperature, followed by a temperature increase to or above the initiation temperature, thus providing a product containing little or no by-product.

U.S. Pat. No. 4,234,435 discloses carboxylic acid acylating agents derived from polyalkenes and a carboxylic reactant having a molecular weight from about 1,300 to 5,000 and having at least 1.3 carboxylic groups per equivalent of polyalkene.

U.S. Pat. No. 4,320,019 discloses a multipurpose lubricating additive prepared by the reaction of an interpolymer of ethylene and a $C_3$ to $C_8$ alpha-monoolefin with an olefinic carboxylic acid acylating agent to form an acylating reaction intermediate that is then reacted with an amine.

U.S. Pat. No. 4,340,689 discloses a process for grafting a functional organic group onto an ethylene copolymer or an ethylene-propylene-diene terpolymer.

U.S. Pat. No. 4,357,250 discloses a reaction product of a copolymer and an olefin carboxylic acid via the "ene" reaction followed by a reaction with monoamine-polyamine mixture.

U.S. Pat. No. 4,382,007 discloses a dispersant-viscosity index improver prepared by reacting a polyamine-derived dispersant with an oxidized ethylene-propylene polymer or an ethylene-propylene-diene terpolymer.

U.S. Pat. No. 4,668,834 discloses low molecular weight copolymers comprised of ethylene, an alphaolefin and, optionally, a nonconjugated polyene, which copolymers have a viscosity index of at least about 75 and vinylidene-type unsaturation. The copolymers are said to possess unexpected advantages as intermediates in epoxy-grafted electrical encapsulation compositions.

U.S. Pat. Nos. 4,797,511 and 4,837,259 describe synergistic blends of hindered phenols and amine antioxidants as stabilizers for polypropylene and polyethylene.

U.S. Pat. No. 4,863,623 discloses multifunctional grafted and derivatized copolymers that provide viscosity index improvement, dispersancy, and antioxidant properties in a multigrade lubricating oil composition. The additive composition comprises a graft and amine-derivatized copolymer prepared from ethylene and at least one $C_3$ to $C_{10}$ alpha-monoolefin and, optionally, a polyene selected from non-conjugated dienes and trienes comprising from about 15 to 80 mole percent of ethylene, from about 20 to 85 mole percent of the $C_3$ to $C_{10}$ alpha-monoolefin, and from about 0 to 15 mole percent of the polyene having an average molecular weight ranging from about 5,000 to 500,000, which has been reacted with at least one olefinic carboxylic acid acylating agent to one or more acylating reaction intermediates characterized by having a carboxylic acid acylating function within their structure and reacting the reaction intermediate with an amino-aromatic polyamine compound. The amino-aromatic polyamine compound is a member selected from the group consisting of an N-arylphenylenediamine, an aminothiazole, an amino carbazole, an aminoindole, an aminopyrrole, an amino indazolinone, an aminomercaptotriazole, and an aminoperimidine to form the graft and amine-derivatized copolymer. A lubricating oil composition containing the additive is also disclosed.

U.S. Pat. No. 4,904,403 discloses compounds derived from 2,5-dimercapto-1,3,4-thiadiazole and one or two moles of polyolefin having 5 to 400 carbon atoms. The 5-position of the 2-mercapto-1,3,4-thiadiazole can be substituted by an alkylthio, a 2-hydroxyalkylthio, an amino, or a hydroxy group. The compounds are said to be effective dispersants, antiwear agents, and antioxidants when incorporated into lubricating compositions.

U.S. Pat. No. 4,990,274 discloses an oil additive composition comprising (1) a mixture of a graft and derivatized polymer and a mineral oil of lubricating viscosity said mixture comprising from about 5 to 35 weight percent of said polymer and the balance said mineral oil and having a bulk viscosity measured as the Kinematic Viscosity at 100° C. above about 2000 Centistokes, and (2) a minor amount of a co-solvent of defined structure effective for substantially reducing the bulk viscosity of said mixture.

U.S. Pat. No. 5,021,177 discloses dispersant viscosity index improvers for lubricating oils containing and EPR or EPT polymer onto which has been graft polymerized with isocyanatoethyl methacrylate and thereafter reacted with N-phenyl-p-phenylene diamine.

U.S. Pat. No. 5,047,530 discloses tris(N-alkyl-p-phenylenediamino)-1,3,5-triazine compounds useful as antiozonants for unsaturated high polymers. The compounds can be prepared by reacting N-alkylphenylenediamine with a cyanuric halide.

U.S. Pat. No. 5,075,383 discloses an additive composition comprising a graft and amine-derivatized copolymer prepared from ethylene and at least one $C_3$ to $C_{10}$ alpha-monoolefin and, optionally, a polyene selected from non-conjugated dienes and trienes comprising from about 15 to 80 mole percent of ethylene, from about 20 to 85 mole percent of the $C_3$ to $C_{10}$ alpha-monoolefin and from about 0 to 15 mole percent of the polyene. The copolymer has an average molecular weight ranging from about 5,500 to 50,000 and has grafted thereon at least 1.8 molecules of a carboxylic acid acylating function per molecule of the copolymer. The grafted copolymer is reacted with an amino-aromatic polyamine compound from the group consisting of an N-arylphenylenediamine, an aminocarbazole, and an aminoperimidine to form the graft and amine-derivatized copolymer. A lubricating oil composition containing the additive is also disclosed.

U.S. Pat. No. 5,094,766 discloses dispersant and antioxidant viscosity index improvers for lubricating oils containing and EPR or EPT polymer onto which has been graft polymerized with vinyl azlactone and thereafter reacted with N-phenyl-p-phenylene diamine.

U.S. Pat. No. 5,120,844 discloses tris-substituted 1,3,5-triazine compounds having at least one (N-alkyl-p-phenylenediamino) group on the triazine ring. The preferred compositions are tri-substituted with the alkyl p-phenylenediamino group. The preferred compounds can be prepared by reacting N-alkylphenylenediamine with a cyanuric halide.

U.S. Pat. No. 5,162,086 discloses an additive composition comprising a graft and amine-derivatized copolymer prepared from ethylene and at least one $C_3$ to $C_{10}$ alpha-monoolefin and, optionally, a polyene selected from non-conjugated dienes and trienes comprising from about 15 to 80 mole percent of ethylene, from about 20 to 85 mole percent of the $C_3$ to $C_{10}$ alpha-monoolefin and from about 0 to 15 mole percent of the polyene. The copolymer has a number average molecular weight ranging from about 5,500 to 50,000 and has grafted thereon at least 1.8 molecules of a carboxylic acid acylating function per molecule of the copolymer. The grafted copolymer is reacted with an amine substituted phenothiazine to form the graft and amine-derivatized copolymer. A lubricating oil composition containing the additive is also disclosed.

U.S. Pat. No. 5,188,745 discloses an additive composition comprising a graft and amine-derivatized copolymer prepared from ethylene and at least one $C_3$ to $C_{10}$ alpha-monoolefin and, optionally, a polyene selected from non-conjugated dienes and trienes comprising from about 15 to 80 mole percent of ethylene, from about 20 to 85 mole percent of the $C_3$ to $C_{10}$ alpha-monoolefin, and from about 0 to 15 mole percent of the polyene. The copolymer has an average molecular weight ranging from about 5,500 to 500,000 and has been reacted with at least one olefinic carboxylic acid acylating agent to form one or more acylating reaction intermediates characterized by having a carboxylic acid acylating function within their structure. This reaction intermediate is then reacted with an N-(2-aminoalkyl)imidazolidone to form the graft derivatized copolymer. A lubricating oil composition containing the additive is also disclosed.

U.S. Pat. No. 5,200,102 discloses an additive composition comprising a graft and derivatized copolymer prepared from ethylene and at least one $C_3$ to $C_{10}$ alpha-monoolefin and, optionally, a polyene selected from non-conjugated dienes and trienes comprising from about 15 to 80 mole percent of ethylene, from about 20 to 85 mole percent of the $C_3$ to $C_{10}$ alpha-monoolefin and from about 0 to 15 mole percent of the polyene having an average molecular weight ranging from about 5,000 to 500,000, which has been reacted with at least one olefinic carboxylic acid acylating agent to form one or more acylating reaction intermediates characterized by having a carboxylic acid acylating function within their structure. The reaction intermediate is reacted with an amino alkylthio thiadiazole to form the graft derivatized copolymer. A lubricating oil composition containing the graft derivatized copolymer is also disclosed.

U.S. Pat. No. 5,474,694 discloses an additive composition comprising a graft and amine-derivatized copolymer prepared from ethylene and at least one $C_3$ to $C_{10}$ alpha-monoolefin and, optionally, a polyene selected from non-conjugated dienes and trienes comprising from about 15 to 80 mole percent of ethylene, from about 20 to 85 mole percent of the $C_3$ to $C_{10}$ alpha-monoolefin, and from about 0 to 15 mole percent of the polyene. The copolymer has a number average molecular weight ranging from about 5,500 to 50,000 and has grafted thereon at least 1.8 molecules of a carboxylic acid acylating function per molecule of the copolymer. The grafted copolymer is reacted with an amino alcohol compound selected from the group consisting of a 2-anilinoalcohol, a (2-hydroxyalkyl)pyridine, a 4-(2-hydroxyalkyl)morpholine, a 1-(2-hydroxyalkyl)piperazine, and a 1-(2-hydroxyalkyl)2-pyrrolidine.

U.S. Pat. No. 5,556,923 discloses a continuous process for producing a adducted derivatized EPM or EPDM oil solution, in which a grafted ethylene polymer is adducted with an antioxidant diamine for formation of an adduct during holding.

U.S. Pat. No. 5,698,500 discloses a graft copolymer prepared by the interpolymerization of a mixture of monomers comprising ethylene, a $C_3$ to $C_{12}$ alpha monoolefin, and a polyene being a member selected from the group consisting of non-conjugated dienes and trienes. Grafted to the copolymer is a 2-mercapto-1,3,4-thiadiazole moiety. Lubricating oil additives and lubricating oils comprising the graft copolymer are also disclosed.

U.S. Pat. No. 5,747,433 discloses a composition of about 2 to about 20 percent of a hydrogenated diene/vinyl aromatic block copolymer and a non-ionic surface active agent, soluble in said oil, comprising at least one ester or ether group, in a medium of oil of lubricating viscosity that is said to exhibit reduced viscosity compared with comparable compositions without the surface active agent.

U.S. Pat. No. 5,834,544 discloses compounds containing dual substitutions of an aromatic amine and hindered phenol functionality that are useful as stabilizers for organic materials.

U.S. Pat. No. 6,107,257 discloses an additive comprising a highly grafted, multi-functional olefin copolymer comprising a graft and amine-derivatized copolymer prepared from ethylene and at least one $C_3$ to $C_{23}$ alpha-monoolefin and, optionally, a polyene, wherein the copolymer of ethylene and at least one $C_3$ to $C_{23}$ alpha-monoolefin has grafted thereon from 0.3 to 0.75 carboxylic groups per 1000 number average molecular weight units of olefin copolymer and wherein the olefin copolymer has a number average molecular weight of between 20,000 and 150,000, and lubricating oil concentrates and compositions containing the same.

U.S. Pat. No. 6,107,258 discloses a multi-functional fuel and lubricant additive that is said to provide dispersancy properties as well as viscosity index improved credit, improved fuel economy and low temperature viscometric properties. Concentrates, fuel and lubricating oil compositions containing said additive are also disclosed.

U.S. Pat. No. 6,117,825 discloses a lubricating oil composition comprising: (a) a major amount of an oil of lubricating viscosity; and (b) a minor dispersant amount of a synergistic combination of an antioxidant-dispersant additive and a dispersant additive, said combination comprising: (i) a polyisobutylene succinimide; and (ii) an ethylene-propylene succinimide.

EP 0 922 752 A2 discloses an olefin copolymer which comprises the reaction product of an acylated olefin copolymer and a polyamine, wherein the acylated olefin copolymer comprises an olefin copolymer having grafted thereon from 0.3 to 0.75 carboxylic groups per 1000 number average molecular weight units of olefin copolymer and wherein the olefin copolymer has a number average molecular weight of from 20,000 to 150,000. The copolymer is used as an additive in lubricating oil compositions where it acts as a viscosity modifier.

The disclosures of the foregoing are incorporated herein by reference in their entirety.

SUMMARY OF THE INVENTION

An object of this invention is to provide a novel antioxidant for the protection of organic materials, such as rubber, plastic, lubricating oils, petroleum fuels, waxes, and organic liquids.

Another object of this invention is to provide a novel antioxidant-bound copolymer composition comprising the novel antioxidant as a moiety thereof.

Still another object of this invention is to provide a lubricant additive effective for imparting viscosity index, dispersancy, and anti-oxidant properties to a lubricating oil composition.

These and other objects, which will be apparent to those skilled in the art, are provided by the present invention, which is directed to a class of antioxidant dispersant additives having viscosity index improving credit that are useful as such or bound to a polymer backbone, e.g., an EPDM copolymer.

More particularly, the present invention is directed to a composition of matter comprising an N-aromatic substituted acid amide compound selected from the group consisting of compounds of the formula:

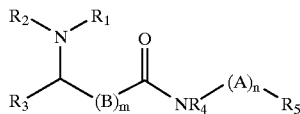

wherein
A and B are independently selected alkylene groups;
$R_1$ is selected from the group consisting of hydrogen, alkyl, alkylether, or ester;
$R_2$ is hydrogen if $R_1$ is hydrogen;
$R_2$ is an alkyl primary amine if $R_1$ is alkyl, alkylether, or ester;
$R_3$ and $R_4$ are independently selected from the group consisting of hydrogen and alkyl;
$R_5$ is a sterically hindered phenolic group,

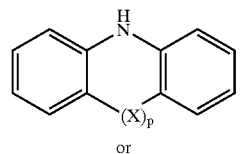

or

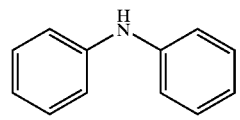

wherein
X is $CH_2$, S, NH, or O; and
m, n, and p are independently selected integers equal to 0 or 1.

It is noted here that any use of the term "alkyl" in the context of a starting material or the final compounds of this invention is deemed to include linear or branched cycloalkyl and alkyl substituted cycloalkyl structures as well; for example, cyclopentyl, cyclohexyl, 4-methylcyclohexyl, and the like.

In another aspect, the present invention is directed to the reaction product comprised of a carboxylic acid material bound to a substantially linear polymer, copolymer, or terpolymer, further reacted with an N-aromatic substituted acid amide moiety selected from the group consisting of compounds of the formula:

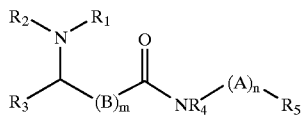

wherein
A and B are independently selected alkylene groups;
$R_1$ is selected from the group consisting of hydrogen, alkyl, alkylether, or ester;
$R_2$ is hydrogen if $R_1$ is hydrogen;
$R_2$ is an alkyl primary amine if $R_1$ is alkyl, alkylether, or ester;
$R_3$ and $R_4$ are independently selected from the group consisting of hydrogen and alkyl;
$R_5$ is a sterically hindered phenolic group,

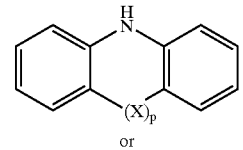

or

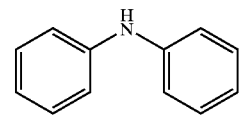

wherein
X is $CH_2$, S, NH, or O; and
m, n, and p are independently selected integers equal to 0 or 1.

In still another aspect, the present invention is directed to a lubricating oil composition comprising a major portion of lubricating oil and a minor portion of an additive that is an N-aromatic substituted acid amide compound or the reaction product comprised of a carboxylic acid material bound to a substantially linear polymer, copolymer, or terpolymer, further reacted with an N-aromatic substituted acid amide moiety, wherein said N-aromatic substituted acid amide is selected from the group consisting of compounds of the formula:

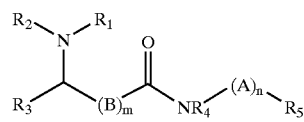

wherein
A and B are independently selected alkylene groups;
$R_1$ is selected from the group consisting of hydrogen, alkyl, alkylether, or ester;
$R_2$ is hydrogen if $R_1$ is hydrogen;
$R_2$ is an alkyl primary amine if $R_1$ is alkyl, alkylether, or ester;
$R_3$ and $R_4$ are independently selected from the group consisting of hydrogen and alkyl;
$R_5$ is a sterically hindered phenolic group,

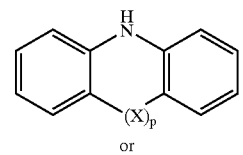

or

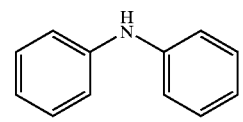

wherein
X is $CH_2$, S, NH, or O; and
m, n, and p are independently selected integers equal to 0 or 1.

In still another aspect, the present invention is directed to a composition of matter comprising a solution comprising:

A) a reaction product comprised of a carboxylic acid material bound to a substantially linear polymer, copolymer, or terpolymer, further reacted with an N-alkyl imidazole;

B) and oil solvent; and

C) a co-solvent comprising an alkyl, dialkyl, or mixed dialkyl phenol, wherein the alkyl group is selected from the group consisting of alkyls of from 6 to 22 carbon atoms.

DESCRIPTION OF THE PREFERRED EMBODIMENTS

As disclosed above, in a preferred embodiment, the present invention is directed to N-aromatic substituted acid amide compounds selected from the group consisting of compounds of the formula:

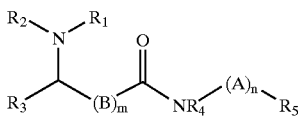

wherein

A and B are independently selected alkylene groups;
$R_1$ is selected from the group consisting of hydrogen, alkyl, alkylether, or ester;
$R_2$ is hydrogen if $R_1$ is hydrogen;
$R_2$ is an alkyl primary amine if $R_1$ is alkyl, alkylether, or ester;
$R_3$ and $R_4$ are independently selected from the group consisting of hydrogen and alkyl;
$R_5$ is a sterically hindered phenolic group,

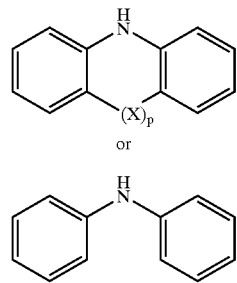

wherein
X is $CH_2$, S, NH, or O; and
m, n, and p are independently selected integers equal to 0 or 1.

These compounds can be used as such or can be reacted with a carboxylic acid material bound to a substantially linear polymer, copolymer, or terpolymer. Such compounds are expected to be useful as antioxidants in compounded tires, polyols, plastics, urethanes, greases, motor oils, rubber belts, cables, gaskets, seals, and rubber products in the garment and carpet industries. When attached to a carbon-carbon polymer backbone, they are also expected to be useful for products that require antioxidants bound to polymers through polymer bound linkage groups, such as succinic or maleic anhydride and epoxides, to prevent antioxidant blooming (see, for example, Kuczkowski, J. A. et al., *Rubber Chemistry and Technology* 57:621(1984)) from the substrate or for polymer property improvement. Examples of products that may use polymer bound antioxidants are automotive tires, beverage bottles, and automotive motor oil polymer additives (see, for example, Mishra, M. K. et al., *Polym. Sci., {Symp. Proc. Polym. '91}*, Vol.2, 694–9. Publisher: Tata McGraw-Hill, New Delhi, India), such as dispersants and viscosity index improvers (see, for example, European Patent Application 98310091.8 and U.S. Pat. Nos. 5,075,383 and 4,863,623). With respect to dispersants, the use of co-solvents to control product viscosity and use in manufacturing processes, outlined in U.S. Pat. Nos. 4,990,274 and 5,556,923, may also be employed with these new derivatizing antioxidant amines.

In the above structural formula, where any of $R_1$, $R_3$, and/or $R_4$ are alkyl, they are preferably alkyl of from 1 to 22 carbon atoms, e.g., methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, uneicosyl, doeicosyl, or isomers thereof, for example, isopropyl, isobutyl, sec-butyl, tert-butyl, 2-ethylhexyl, and the like. It is more preferred that where $R_1$ is alkyl, it is alkyl of from 8 to 18 carbon atoms, most preferred that it be of from 8 to 14 carbon atoms. It is more preferred that $R_3$ and $R_4$ be independently selected from the group consisting of hydrogen and alkyl of 1 to 6 carbon atoms, most preferred that $R_3$ be of from 1 to 6 carbon atoms and $R_4$ be hydrogen. Similarly, where $R_2$ is an alkyl primary amine, the alkyl portion thereof is preferably alkyl of from 1 to 22 carbon atoms, where any carbon-carbon chain can be either linear or branched.

Where B is present in the molecule, it is preferably alkylene of from 1 to 22 carbon atoms, e.g., methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, uneicosylene, doeicosylene and isomers thereof, i.e., it can be unbranched or branched, for example, isopropylene, isobutylene, 2-ethylhexylene, and the like. It is more preferred that it be of from 1 to 12 carbon atoms, most preferred that it be of from 1 to 6 carbon atoms. Where B is present, it is preferably methylene. Those skilled in the art will understand that these structures are, for example, —$CH_2$—, —$CH_2$—$CH_2$—, —$CH_2$—$CH_2$—$CH_2$—, etc.

Where $R_1$ is alkylether or ester, it is similarly preferred that the total number of carbon atoms in the moiety be in the range of from 2 to 22.

Where $R_5$ is a sterically hindered phenolic group, it is preferably of the structure

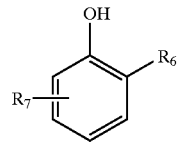

wherein $R_6$ is alkyl of from 3 to 22 carbon atoms and $R_7$ is hydrogen or alkyl of from 1 to 22 carbon atoms. Thus, $R_6$ can be, e.g., propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, uneicosyl, doeicosyl, or isomers thereof, for example, isopropyl, isobutyl, sec-butyl, tert-butyl, 2-ethylhexyl, and the like. It is more preferred that $R_6$ be alkyl of from 4 to 18 carbon atoms, most preferred that it be of from 4 to 14 carbon atoms. $R_7$ is hydrogen or alkyl of from 1 to 22 carbon atoms. Where $R_7$ is alkyl, it can be, e.g., methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, uneicosyl, doeicosyl, or isomers thereof, for example, isopropyl, isobutyl, sec-butyl, tert-butyl, 2-ethylhexyl, and the like. It is preferred that $R_7$ be hydrogen or alkyl of 1 to 18 carbon atoms, most preferred that $R_7$ be alkyl of from 1 to 14 carbon atoms.

In the above structural formulae, m, n, and p are independently selected integers equal to 0 or 1. By this, it is meant that the moieties within the parentheses that precede them are either present, where a given integer is 1, or absent, where the integer is 0. Where m, n, and p are all equal to 0, the structural formula reduces to, for example,

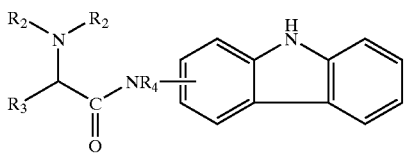

The compounds, in a preferred embodiment of the present invention, can be divided into two groups based on chemical structure, i.e., (A) those compounds where both $R_1$ and $R_2$ are hydrogen, e.g.,

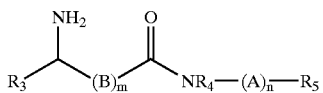

and (B) those compounds where $R_1$ is $C_1$–$C_{22}$ branched or linear alkyl (or alkylene) and $R_2$ an alkyl primary amine, such as —$CH_2CH_2$—$NH_2$ or —$CH_2CH_{12}CH_2$—$NH_2$, e.g.,

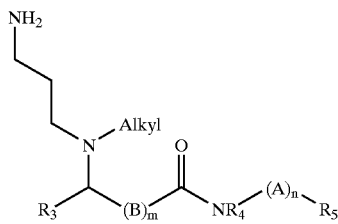

Both of these compounds are derived from the same starting compounds of the following structure:

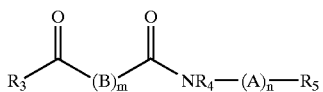

Antioxidants of group (A) are prepared by catalytic reductive amination of the starting compound above with ammonia and hydrogen. The antioxidants of group (B) are prepared by reacting the starting compounds above with an N-alkyl cyanoalkylamine, e.g., the N-alkyl cyanoethylamine shown below

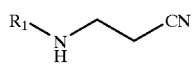

to form the imine adduct intermediate, which is then catalytically hydrogenated to the final product.

As pointed out above, the N-aromatic substituted acid amide compounds of the present invention can be used as such or can be reacted with a carboxylic acid material bound to a substantially linear polymer, copolymer, or terpolymer. The polymer backbone can be prepared from ethylene and propylene or it can be prepared from ethylene and at least one higher olefin within the range of $C_3$ to $C_{23}$ alpha-olefins.

Other alpha-olefins suitable in place of propylene to form the copolymer or to be used in combination with ethylene and propylene to form a terpolymer include 1-butene, 1-pentene, 1-hexene, 1-octene, and styrene; α,ω-diolefins, such as 1,5-hexadiene, 1,6-heptadiene, 1,7-octadiene; branched chain α-olefins, such as 4-methylbutene-1,5-methylpentene-1, and 6-methylheptene-1; and mixtures thereof.

More complex polymer substrates, often designated as interpolymers, may be prepared using a third component. The third component generally used to prepare an interpolymer substrate is a polyene monomer selected from non-conjugated dienes and trienes. The non-conjugated diene component is one having from 5 to 14 carbon atoms in the chain. Preferably, the diene monomer is characterized by the presence of a vinyl group in its structure and can include cyclic and bicyclo compounds. Representative dienes include 1,4-hexadiene, 1,4-cyclohexadiene, dicyclopentadiene, 5-ethylidene-2-norbornene, 5-methylene-2-norbornene, 1,5-heptadiene, and 1,6-octadiene. A mixture of more than one diene can be used in the preparation of the interpolymer. A preferred non-conjugated diene for preparing a terpolymer or interpolymer substrate is 1,4-hexadiene.

The triene component will have at least two non-conjugated double bonds, and up to about 30 carbon atoms in the chain. Typical trienes useful in preparing the interpolymer of the invention are 1-isopropylidene-3α,4,7,7α-tetrahydroindene, 1-isopropylidenedicyclopentadiene, dihydro-isodicyclopentadiene, and 2-(2-methylene-4-methyl-3-pentenyl)[2.2.1]bicyclo-5-heptene.

Ethylene-propylene or higher alpha-olefin copolymers may consist of from about 15 to about 80 mole percent ethylene and from about 85 to about 20 mole percent $C_3$ to $C_{23}$ α-olefin with the preferred mole ratios being from about 35 to 75 mole percent ethylene and from about 65 to 25 mole percent of the $C_3$ to $C_{23}$ α-olefin, with the more preferred proportions being from 50 to 70 mole percent ethylene and 50 to 30 mole percent of the $C_3$ to $C_{23}$ α-olefin, and the most preferred proportions being from 55 to 65 mole percent ethylene and 45 to 35 mole percent of the $C_3$ to $C_{23}$ α-olefin.

Terpolymer variations of the foregoing polymers can contain from about 0.1 to about 10 mole percent of a non-conjugated diene or triene.

The ethylene copolymer or terpolymer substrate is an oil-soluble, linear or branched polymer having a number average molecular weight of from about 20,000 to about 150,000 as determined by gel permeation chromatography and universal calibration standardization, with a preferred number average molecular weight range of 30,000 to 110,000.

The terms polymer and copolymer are used generically to encompass ethylene copolymers, terpolymers, or interpolymers. These materials can contain minor amounts of other olefinic monomers provided the basic characteristics of the ethylene copolymers are not materially changed.

The polymerization reaction used to form the ethylene-olefin copolymer substrate is generally carried out in the presence of a conventional Ziegler-Natta or metallocene catalyst system. The polymerization medium is not specific and can include solution, slurry, or gas phase processes, all known to those skilled in the art. When solution polymerization is employed, the solvent may be any suitable inert hydrocarbon solvent that is liquid under reaction conditions for polymerization of α-olefins. Examples of satisfactory hydrocarbon solvents include straight chain paraffins having from 5 to 8 carbon atoms, with hexane being preferred. Aromatic hydrocarbons, preferably aromatic hydrocarbons having a single benzene nucleus, such as benzene, toluene, and the like, and saturated cyclic hydrocarbons having boiling point ranges approximating those of the straight chain paraffinic hydrocarbons and aromatic hydrocarbons, described above, are particularly suitable. The solvent selected can be a mixture of one or more of the foregoing hydrocarbons. When slurry polymerization is employed, the liquid phase for polymerization is preferably liquid propylene. It is desirable that the polymerization medium be free of substances that will interfere with the catalyst components.

Next, an ethylenically unsaturated carboxylic acid material is grafted onto the prescribed polymer backbone to form an acylated ethylene copolymer. Those materials suitable for grafting onto the backbone contain at least one ethylenic bond and at least one, preferably two, carboxylic acid or its anhydride groups, or a polar group that is convertible into a carboxyl group by oxidation or hydrolysis. Preferably, the carboxylic acid reactants are selected from the group consisting of acrylic, methacrylic, cinnamic, crotonic, maleic, fumaric, and itaconic reactants. More preferably, the carboxylic reactants are selected from the group consisting of maleic acid, fumaric acid, maleic anhydride, and mixtures thereof. Maleic anhydride or a derivative thereof is generally most preferred owing to its commercial availability and ease of reaction. In the case of unsaturated ethylene copolymers or terpolymers, itaconic acid or its anhydride is preferred owing to its reduced tendency to form a cross-linked structure during the free-radical grafting process.

The ethylenically unsaturated carboxylic acid materials typically can provide one or two carboxylic groups per mole of reactant to the grafted polymer. For example, methyl methacrylate can provide one carboxylic group per molecule to the grafted polymer, while maleic anhydride can provide two.

The carboxylic reactant is grafted onto the prescribed polymer backbone in an amount to provide from about 0.3 to about 0.75 carboxylic groups per 1000 number average molecular weight units of the polymer backbone, preferably from about 0.3 to about 0.5 carboxylic groups per 1000 number average molecular weight. For example, a copolymer substrate with an M, of 20,000 would be grafted with from about 6 to about 15 carboxylic groups per polymer chain, or from about 3 to about 7.5 moles of maleic anhydride per mole of polymer, whereas a copolymer having an $M_n$ of 100,000 would be grafted with from about 30 to about 75 carboxylic groups per polymer chain, or from about 15 to about 37.5 moles of maleic anhydride per polymer chain. The minimum level of functionality is the level needed to achieve the minimum satisfactory dispersancy performance. Above the maximum functionality level little, if any, additional dispersancy performance is noted and other properties of the additive may be adversely affected.

The grafting reaction to form the acylated olefin copolymers is generally carried out using a free-radical initiator either in solution or in bulk, as in an extruder or intensive mixing device. When the polymerization is carried out in hexane solution, it is economically convenient to carry out the grafting reaction as described in U.S. Pat. Nos. 4,340,689; 4,670,515; and 4,948,842, incorporated herein by reference. The resulting polymer intermediate is characterized by having carboxylic acid acylating functionality randomly distributed throughout its structure.

In the bulk process for forming the acylated olefin copolymers, one feeds the olefin copolymer to rubber or plastic processing equipment, such as an extruder or an intensive mixer or masticator, heats to a temperature of about 150° to about 400° C., and co-feeds the ethylenically unsaturated carboxylic acid reagent and free-radical initiator to the molten polymer to effect grafting. Optionally, the reaction can be carried out using mixing conditions to effect shearing and grafting of the ethylene copolymers as described in U.S. Pat. No. 5,075,383, incorporated herein by reference. The processing equipment is generally purged with nitrogen to prevent oxidation of the polymer and to aid in venting unreacted reagents and byproducts of the grafting reaction. The residence time in the processing equipment is sufficient to provide for the desired degree of acylation and to allow for purification of the acylated copolymer via venting. Optionally, mineral or synthetic lubricating oil can be added to the processing equipment after the venting stage to dissolve the acylated copolymer.

The free-radical initiators that can be used to graft the ethylenically unsaturated carboxylic acid material to the polymer backbone include peroxides, hydroperoxides, peresters, and azo compounds, preferably those that have a boiling point greater than 100° C. and that thermally decompose to provide free radicals within the grafting temperature range. Representative free-radical initiators include azobutyronitrile, dicumyl peroxide, 2,5-dimethylhexane-2, 5-bis-tertiarybutyl peroxide, and 2,5-dimethylhex-3-yne-2, 5-bis-tertiarybutyl peroxide. The initiator is used in an amount of between about 0.005% and about 1% by weight, based on the weight of the reaction mixture.

Other methods known in the art for effecting reaction of ethylene-olefin copolymers with ethylenically unsaturated carboxylic reagents, such as halogenation reactions, thermal, or "ene" reactions, or mixtures thereof, can be used instead of the free-radical grafting process. Such reactions are conveniently carried out in mineral oil or bulk by heating the reactants at temperatures of from about 250° to about 400° C. under an inert atmosphere to avoid the generation of free radicals and oxidation byproducts. "Ene" reactions are a preferred method of grafting when the ethylene-olefin copolymer contains unsaturation. To achieve graft levels of from about 0.3 to about 0.75 carboxylic groups per 1000 $M_n$, it may be necessary to follow or precede the "ene" or thermal graft reaction with a free radical graft reaction.

The reaction between the carboxylic acid material bound to a substantially linear polymer, copolymer, or terpolymer and the N-aromatic substituted acid amide compounds of the present invention is conducted by heating a solution of the polymer substrate under inert conditions and then adding the N-aromatic substituted acid amide compound to the heated solution, generally with mixing to effect the reaction. It is convenient to employ an oil solution of the polymer substrate heated to 140° to 175° C., while maintaining the solution under an inert atmosphere or a nitrogen blanket. The N-aromatic substituted acid amide compound is added to this solution and the reaction is effected under the noted conditions. The N-aromatic substituted acid amide compound can be added in one of two ways—neat or in a solution of suitable carrier solvent capable of delivering said compound into the reaction vessel, such as oil, toluene, or dinonyl phenol.

As disclosed in U.S. Pat. No. 4,990,274, it is possible to reduce the bulk viscosity of a mixture of graft and derivatized polymer in mineral oil with the addition of a minor amount of co-solvent such as an ethoxylated alcohol, polypropylene glycol, or adipate diester. It has now been discovered that the addition of dinonyl phenol also has the benefit of reducing the bulk viscosity of the finished product. The co-solvent may be added prior to, with, or following the addition of the acid amide compound. In addition, this effect is evident regardless of what the derivatizing agent is. Examples of other derivatizing agents are polyamines, hydroxyamines, or polyols. Particularly useful polyamines are those having from 2 to 20 carbon atoms and 2 to 5 nitrogen atoms in the molecule where only one nitrogen atom is a primary nitrogen atom and all the rest are tertiary nitrogen atoms or highly hindered secondary nitrogen atoms. The class of suitable polyamines includes: hydrocarbyl polyamines including alkyl, aryl and mixed alkaryl polyamines, which may contain additional groups, such as hydroxy, oxyamide and imidazoline groups, N-phenyl-phenylenediamine, N-amino alkylimidazole, or N-amino alkyl morpholine. Useful hydroxyamines are those hydroxyamines having from 2 to 20 carbon atoms, 1 to 4 hydroxy groups and 1 to 5 nitrogen atoms. Typical hydroxyamines include: diethanolamine, di-propanolamine, tris-hydroxymethyl amino-methane and 2-amino-2-ethyl-1, 3-propanediol. Useful polyols for the derivatization reaction are the polyols having from 2 to 20 carbon atoms and having from 2 to 5 hydroxyl groups. Typical polyols include glycerol and alkylene glycols, such as dipropylene glycol and pentaerythritol.

The novel grafted polymers of the invention are useful as additives for lubricating oils. They are multi-functional additives for lubricants being effective to provide dispersancy, viscosity index improvement, and anti-oxidant properties to lubricating oils. They can be employed in a variety of oils of lubricating viscosity, including natural and synthetic lubricating oils and mixtures thereof. The novel additives can be employed in crankcase lubricating oils for spark-ignited and compression-ignited internal combustion engines. The compositions can also be used in gas engines, or turbines, automatic transmission fluids, gear lubricants, metal-working lubricants, hydraulic fluids, and other lubricating oil and grease compositions. Their use in motor fuel compositions is also contemplated.

For certain applications, such as single grade lubricating oils, it may be desirable to reduce the molecular weight of the polymers. The reduction of the molecular weight of the starting ethylene copolymer having a molecular weight above 80,000 to a molecular weight ranging from 5,500 to 80,000 and the grafting of the ethylenically unsaturated carboxylic acid material onto the copolymer may be accomplished simultaneously or it may be accomplished sequentially in any order. If done sequentially, the ethylene copolymer can first be degraded to the prescribed molecular weight and then grafted or, conversely, the grafting can be effected onto the high molecular weight copolymer and the resulting high molecular weight grafted copolymer then reduced in molecular weight. Alternatively, grafting and reduction of the high molecular weight copolymer can be done simultaneously.

Reduction of the molecular weight of the high molecular weight ethylene copolymer to the prescribed molecular weight range is conducted in the absence of a solvent or in the presence of a base oil, using a mechanical shearing means. Generally, the ethylene copolymer is heated to a molten condition at a temperature in the range of 250° C. to 450° C. and it is then subjected to mechanical shearing means until the copolymer is reduced to the prescribed molecular weight range. The shearing may be effected by forcing the molten copolymer through fine orifices under pressure or by other mechanical means.

The additives of this invention can be used in combination with other additives typically found in lubricating oils, and such combinations may, in fact, provide synergistic effects toward improving desired properties, such as improved deposit control, anti-wear, frictional, antioxidant, low temperature, and like properties, to the lubricating oil. The typical additives found in lubricating oils are dispersants, detergents, rust inhibitors, antioxidants, antiwear agents, antifoamants, friction modifiers, seal swell agents, demulsifiers, VI improvers, and pour point depressants. See, e.g., U.S. Pat. No. 5,498,809 for a description of useful lubricating oil composition additives. Examples of dispersants include polyisobutylene succinimides, polyisobutylene succinate esters, Mannich Base ashless dispersants, and the like. Examples of detergents include metallic alkyl phenates, sulfurized metallic alkyl phenates, metallic alkyl sulfonates, metallic alkyl salicylates, and the like. Examples of antioxidant additives that can be used in combination with the additives of the present invention include alkylated diphenylamines, N-alkylated phenylendiamines, hindered phenolics, alkylated hydroquinones, hydroxylated thiodiphenyl ethers, alkylidenebisphenols, oil soluble copper compounds, and the like. Examples of anti-wear additives that can be used in combination with the additives of the present invention include organo borates, organo phosphites, organic sulfur-containing compounds, zinc dialkyl dithiophosphates, zinc diaryl dithiophosphates, phosphosulfurized hydrocarbons, and the like. Examples of friction modifiers that can be used in combination with the novel additives of the present invention include fatty acid esters and amides, organo molybdenum compounds, molybdenum dialkylthiocarbamates, molybdenum dialkyl dithiophosphates, and the like. An example of an antifoamant is polysiloxane, and the like. An example of a rust inhibitor is polyoxyalkylene polyols, and the like. Examples of VI improvers include olefin copolymers and dispersant olefin copolymers, and the like. An example of a pour point depressant is polymethacrylate, and the like.

In general, the lubricating oil composition of the invention will contain the novel product in a concentration ranging from about 0.01 to about 30 weight percent. A preferred concentration range for the additive is from about 1 to 15 weight percent based on the total weight of the oil composition. Compositions, when containing these additives, typically are blended into the base oil in amounts that are effective to provide their normal attendant function. Representative effective amounts of such additives are illustrated as follows:

| Compositions | Broad Wt % | Preferred Wt % |
| --- | --- | --- |
| V.I. Improver | 1–12 | 1–4 |
| Corrosion Inhibitor | 0.01–3 | 0.01–1.5 |
| Oxidation Inhibitor | 0.01–5 | 0.01–1.5 |
| Dispersant | 0.1–10 | 0.1–5 |
| Lube Oil Flow Improver | 0.01–2 | 0.01–1.5 |
| Detergents and Rust Inhibitors | 0.01–6 | 0.01–3 |
| Pour Point Depressant | 0.01–1.5 | 0.01–0.5 |
| Anti-Foaming Agents | 0.001–0.1 | 0.001–0.01 |
| Antiwear Agents | 0.001–5 | 0.001–1.5 |
| Seal Swellant | 0.1–8 | 0.1–4 |
| Friction Modifiers | 0.01–3 | 0.01–1.5 |
| Lubricating Base Oil | Balance | Balance |

When other additives are employed, it may be desirable, although not necessary, to prepare additive concentrates comprising concentrated solutions or dispersions of the subject additives of this invention (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of typically from about 2.5 to about 90%, and preferably from about 15 to about 75%, and most preferably from about 25 to about 60% by weight additives in the appropriate proportions with the remainder being base oil. The final formulations may employ typically about 1–20 wt. % of the additive-package with the remainder being base oil.

Oil concentrates of the additives may contain from about 1 to 50 weight percent of the additive reaction product in a carrier or diluent oil of lubricating oil viscosity. If desired, the bulk viscosity of the oil concentrate can be reduced by mixing a minor amount of a co-solvent with the concentrate, as disclosed in U.S. Pat. No. 4,990,274.

All of the weight percents expressed herein (unless otherwise indicated) are based on active ingredient (AI) content of the additive, and/or upon the total weight of any additive-package or formulation, which will be the sum of the (AI) weight of each additive plus the weight of total oil or diluent.

In general, the lubricant compositions of the invention contain the additives in a concentration ranging from about 0.01 to about 30 weight percent. A concentration range for the additives ranging from about 0.01 to about 10 weight percent based on the total weight of the oil composition is preferred. A preferred concentration range is from about 0.2 to about 5 weight percent. Oil concentrates of the additives can contain from about 1 to about 75 weight percent of the additive reaction product in a carrier or diluent oil of lubricating oil viscosity.

In general, the additives of the present invention are useful in a variety of lubricating oil basestocks. The lubricating oil basestock is any natural or synthetic lubricating base oil stock fraction having a kinematic viscosity at 100° C. of about 2 to 200 cSt, more preferably about 3 to 150 cSt, most preferably about 3 to 100 cSt, The lubricating oil basestock can be derived from natural lubricating oils, synthetic lubricating oils, or mixtures thereof. Suitable lubricating oil basestocks include basestocks obtained by isomerization of synthetic wax and wax, as well as hydrocrackate basestocks produced by hydrocracking (rather than solvent extracting) the aromatic and polar components of the crude. Natural lubricating oils include animal oils, vegetable oils (e.g., rapeseed oils, castor oils and lard oil), petroleum oils, mineral oils, and oils derived from coal or shale.

Synthetic oils include hydrocarbon oils and halo-substituted hydrocarbon oils, such as polymerized and interpolymerized olefins, alkylbenzenes, polyphenyls, alkylated diphenyl ethers, alkylated diphenyl ethers, aklylated diphenyl sulfides, as well as their derivatives, analogs, and homologs thereof and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The lubricating oil may be derived from unrefined, refined, rerefined oils, or mixtures thereof. Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to the unrefined oils except that refined oils have been treated in one or more purification steps to improve one or more properties. Suitable purification techniques include distillation, hydrotreating, dewaxing, solvent extraction, acid or base extraction, filtration, and percolation, all of which are known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions of specific viscosity range. Wax isomerate is also characterized by possessing very high viscosity indices, generally having a VI of at least 130, preferably at least 135 and higher and, following dewaxing, a pour point of about −20° C. and lower.

The additives of the present invention are especially useful as components in many different lubricating oil compositions. The additives can be included in a variety of oils with lubricating viscosity including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions.

The advantages and the important features of the present invention will be more apparent from the following examples.

EXAMPLE 1

N-(4-Anilinophenyl)-3-[(3-aminopropyl)-(cocoalkyl)aminio]butanamide

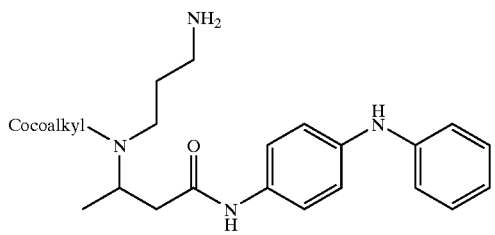

A quantity of 102.4 g. (0.38 mol) of N-(4-anilinophenyl)-3-oxo butanamide, 91.6 g. of N-(cocoalkyl)-3-aminopropanenitrile, and 12 g. of acid-leached bentonite clay were agitated for 48 hours at 130° C. An equal volume of toluene was then charged and refluxed for 30 minutes. This was cooled, filtered, and allowed to stand overnight before filtering again. The mixture was then treated with Raney cobalt catalyst and 800 psi hydrogen gas for 5 hours at 110° C. The catalyst was filtered out and the solvent was stripped off under vacuum. The product (a viscous burgundy oil) was obtained in a yield of 133 g.

EXAMPLE 2

3-Amino-N-(4-anilinophenyl)-butanamide

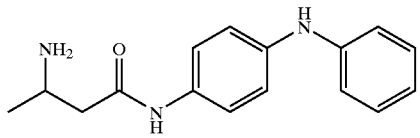

Thirty grams (0.11 mol) of N-(4-anilinophenyl)-3-oxo butanamide was dissolved in 300 ml of toluene. This was mixed with 30 g. (1.8 mol) of anhydrous ammonia, Raney nickel catalyst, and 800 psi of hydrogen gas at a temperature of 70° C. for 2 hours. The catalyst was removed and the solvent stripped off under vacuum. Purification was done by flash chromatography and recrystallization from hot toluene. The product was obtained in a yield of 16 g. with a melting point of 130–132° C.

EXAMPLE 3

3-Amino-N-(4-anilinophenyl)-N-isopropyl butanamide

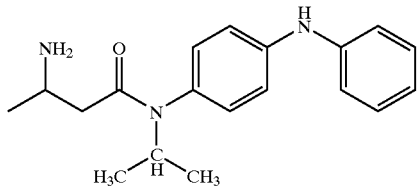

Example 3 is made in a similar fashion to Example 2 starting from N-(4-anilinophenyl)-3-oxo N-isopropyl butanamide. The product has a melting point of 145–151° C.

The starting materials for Examples 1, 2, and 3 can be derived from the reaction product of diketene or acetoacetate ester and the corresponding amine.

EXAMPLE 4

Seventy-five grams of a maleic anhydride graft polymer (rubber), in which the polymer substrate comprised about 57 mole percent ethylene and 43 mole percent propylene having a number average molecular weight of about 22,000, on which has been grafted 2.9 weight percent of maleic anhydride in 225 grams of lubricant diluent oil, was heated to 160° C. with mechanical stirring while the mixture was maintained under a nitrogen blanket. Once temperature was reached, mixing was continued for an additional hour at 160° C.

Eleven grams of N-(4-anilinophenyl)-3-[(3-aminopropyl)-(cocoalkyl) amino]butanamide dissolved in toluene (42%) was added to the oil solution of the polymer and a reaction effected over 4 hours at 160° C. under nitrogen. The reaction mixture containing the derivatized graft polymer was then cooled and filtered.

EXAMPLE 5

Seventy-five grams of a maleic anhydride graft polymer (rubber), in which the polymer substrate comprised about 57 percent ethylene and 43 percent propylene having a number average molecular weight of about 22,000, on which has been grafted 2.9 weight percent of maleic anhydride in 225 grams of lubricant diluent oil, was heated to 160° C. with mechanical stirring while the mixture was maintained under a nitrogen blanket. Once temperature was reached, mixing was continued for an additional hour at 160° C.

A quantity of 5.98 grams of neat 3-amino-N-(4-anilinophenyl)-N-isopropyl butanamide was added to the oil solution of the polymer and a reaction effected over 4 hours at 160° C. under nitrogen. Five grams of dinonyl phenol was added as a co-solvent and the reaction mixture was stirred for an additional hour. The reaction mixture containing the derivatized graft polymer was then cooled and filtered.

EXAMPLE 6

A quantity of 31.25 grams of a maleic anhydride graft polymer (rubber), in which the polymer substrate comprised about 57 percent ethylene and 43 percent propylene having a number average molecular weight of about 22,000, on which has been grafted 2.9 weight percent of maleic anhydride in 88.75 grams of lubricant diluent oil, was heated to 160° C. with mechanical stirring while the mixture was maintained under a nitrogen blanket. Once temperature was reached, mixing was continued for an additional hour at 160° C.

A quantity of 2.88 grams of neat 3-amino-N-(4-anilinophenyl)-butanamide was added to the oil solution of the polymer and a reaction effected over 4 hours at 160° C. under nitrogen. Twelve grams of dinonyl phenol was added as a co-solvent and the reaction mixture was stirred for an additional hour. The reaction mixture containing the derivatized graft polymer was then cooled and filtered.

Oxidation Test

Pressure Differential Scanning Calorimetry Test

PDSC Formulation

The additives were tested for effectiveness in a motor oil formulation (see description in Table 1) and compared to identical formulations with and without any zinc dialkyldithiophosphate (ZDDP).

TABLE 1

SAE 10W-30 Motor Oil Formulation (Base Blend)

| | wt. % |
|---|---|
| Solvent Neutral 100 | Balance |
| Solvent Neutral 150 | 52 |
| Succinimide Dispersant | 4 |
| Overbased Calcium Sulfonate Detergent | 1.3 |
| Rust/Corrosion Inhibitor | 0.3 |
| Antioxidant | 0.0 |
| Pour Point Depressant | 0.1 |
| OCP VI Improver | 5.5 |
| ZDDP | Y |
| Example x | Z |

TABLE 2

Additive concentration

| Example | Description | Y (wt % ZDDP) | Z (wt % example) |
|---|---|---|---|
| Example 7 | Base blend* with ZDDP | 1 | 0 |
| Example 8 | Base blend* with ZDDP | 2 | 0 |
| Example 9 | Base blend* with Example 1 | 0 | 0.03 |
| Example 10 | Base blend* with ZDDP and Example 1 | 1 | .015 |
| Example 11 | Base blend* with Example 2 | 0 | 0.03 |
| Example 12 | Base blend* with ZDDP and Example 2 | 1 | .015 |
| Example 13 | Base blend* with Example 3 | 0 | 0.03 |
| Example 14 | Base blend* with ZDDP and Example 3 | 1 | .015 |
| Example 15 | Base blend* with Example 4 | 0 | 2 |
| Example 16 | Base blend* with ZDDP and Example 4 | 1 | 1 |
| Example 17 | Base blend* with Example 5 | 0 | 2 |
| Example 18 | Base blend* with ZDDP and Example 5 | 1 | 1 |
| Example 19 | Base blend* with Example 6 | 0 | 2 |
| Example 20 | Base blend* with ZDDP and Example 6 | 1 | 1 |

*Note:
Base Blend refers to the formulation in Table 1

The antioxidant properties of the novel reaction products were determined in the Pressure Differential Scanning Calorimetry (PDSC) Test. The PDSC conditions are in Table 3. The PDSC data in Table 4 are a measure of the oxidation induction time (OIT) of each blend. All formulations were blended at 65° C. for 15 minutes under a nitrogen atmosphere. The PDSC method employs a steel bomb under pressure; the catalyst is oil soluble iron derived from iron naphthenate. At the start of a run, the PDSC cell is initially heated at a rate of 40° C./min to the isothermal temperature listed in Table 3. The induction time is measured from the time the sample reaches its isothermal temperature until the enthalpy change is observed. The longer the oxidation induction time, the better the oxidation stability of the oil. The PSDC instrument used is a Mettler DSC27HP, manufactured by Mettler-Toledo, Inc. The test has a repeatability of ±2.5 minutes with 95% confidence for OIT's less than 100 min. Each data point is the average of two runs on a single test blend. A baseline result for the formulation in Table 1 that does not contain ZDDP or DCA-AO could not be determined, as the oil oxidizes prior to reaching the testing temperature of 175° C.

TABLE 3

PDSC Test Parameters

| Test | PDSC |
|---|---|
| Temperature | 175° C. |
| O$_2$ Gas Pressure | 500 psi |
| Flow Through Cell | 100 ml/min. |
| Catalyst | 50 ppm Iron |
| Sample Holder | Open Aluminum Pan |
| Sample Size | 3 mg |
| Induction Time | Enthalpy Change |

TABLE 4

PDSC results

| Example | OIT (min) | Example | OIT (min) |
|---|---|---|---|
| Example 7 | 8.84 | Example 14 | 11.26 |
| Example 8 | 15.60 | Example 15 | 2.83 |
| Example 9 | 1.86 | Example 16 | 13.35 |
| Example 10 | 15.2 | Example 17 | 3.75 |
| Example 11 | 2.7 | Example 18 | 19.08 |
| Example 12 | 14.33 | Example 19 | 2.59 |
| Example 13 | 1.88 | Example 20 | 14.94 |

It can be seen from the above data that the addition of these novel reaction products improves the OIT of the base blend from Table 1. A seen in Example 18, when the novel reaction products are used along with ZDDP, there is a significant boost in performance resulting from the synergy between the reaction product and the ZDDP.

Deposit Control Test
Thermo-oxidative Engine Oil Simulation Test (TEOST)
TEOST Formulation The additives were tested for effectiveness in a motor oil formulation (see description in Table 5) and compared to an identical formulation.

TABLE 5

SAE 10W-30 Motor Oil Formulation (Base Blend)

| | wt. % |
|---|---|
| Solvent Neutral 100 | Balance |
| Overbased Calcium Sulfonate Detergent | 1.3 |
| Rust/Corrosion Inhibitor | 0.75 |
| Antioxidant | 0.5 |
| Pour Point Depressant | 0.1 |
| OCP VI Improver | 5.5 |
| ZDDP | 0.8 |
| Example x | 2.5 |

The Deposit control properties of the novel reaction products were determined in the Thermo-oxidative Engine Oil Simulation Test (TEOST). The test is used to determine the amount of deposits formed by automotive engine oils, and is run as a version of ASTM test D6335-98 with the number of cycles increased to increase the severity of the test.

In this test a sample of engine oil at a temperature of 100° C. that contains ferric naphthenate and is in contact with nitrous oxide and moist air is pumped at a set flow rate past a tared depositor rod. The rod is resistively heated through 9.5 minute temperature cycles that go from 200–480° C. When all cycles are completed the rod is rinsed of oil residue and dried to obtain a gross mass. The oil sample is flushed from the system and passed through a tared filter. The mass of deposits on the rod and filter is the total deposit mass. Performance is measured as total deposit mass in milligrams with results typically between 10 and 100. The lower the number versus the reference, the better the performance of the oil formulation. Table 6 lists the parameters for the TEOST as performed, with results for the mixture of graft and derivatized polymer in mineral oil samples (Examples 4, 5, and 6) found in Table 7 and is the average of two runs on two separate blends.

TABLE 6

TEOST Parameters

| Conditions | Setting |
| --- | --- |
| Reactor Temperature | 100° C. |
| Temperature Cycle | 200–400° C. |
| Number of Cycles | 25 |
| Cycle time | 9.5 min |
| Oil Flow Rate | 0.45 ml/min |
| Oil Volume | 116 ml |
| $N_2O$/moist air Flow Rate | 3.5 ml/min |
| Catalyst (Iron naphthenate) | 100 ppm |

TABLE 7

TEOST Results

| Example | Description | mg deposits | % deposit decrease |
| --- | --- | --- | --- |
| Example 21 | Base Blend** | 59.8 | NA |
| Example 22 | Base Blend** with Example 4 | 26.5 | 55.7 |
| Example 23 | Base Blend** with Example 5 | 29.2 | 51.1 |
| Example 24 | Base Blend** with Example 6 | 36.7 | 38.6 |

**Note:
Base Blend refers to the formulation in Table 5

It can be seen from the above data that the addition of these novel reaction products reduces the total deposit mass of the base blend formulation. For example, the addition of Example 4 to the base blend reduces deposit formation by over 55 percent.

Control of Bulk Viscosity

Reduction in the high bulk viscosities of the oil solution of the grafted and derivatized polymers is achieved by admixing a minor amount of the prescribed co-solvent with the copolymer. In general, an oil concentrate of the grafted and derivatized polymer containing from about 5 to 50 weight percent of the grafted and derivatized polymer dissolved therein and containing from about 0.1 to 15 weight percent of the co-solvent based on the total weight of the concentrate will exhibit substantially improved flow or fluid characteristics for the concentrate mixture. A preferred amount of co-solvent in the concentrate mixture is an amount ranging from about 0.5 to 8 weight percent based on the total weight of the concentrate with the most preferred concentration of the co-solvent being an amount ranging from about 2 to 5 weight percent. A flowable concentrate is obtained by admixing an effective or suitable amount of the co-solvent into the oil concentrate of the final grafted and derivatized polymer or copolymer. The preferred co-solvent is an alkyl, dialkyl, or mixed dialkyl phenol wherein each alkyl group is selected from the group consisting of alkyls of from 6 to 22 carbon atoms, e.g., hexyl, heptyl, octyl, nonyl, decyl, undecyl, dodecyl, tridecyl, tetradecyl, pentadecyl, hexadecyl, heptadecyl, octadecyl, nonadecyl, eicosyl, uneicosyl, doeicosyl, or isomers thereof. The most preferred dialkyl phenol is dinonyl phenol.

Alternatively, the flowable oil concentrate can be prepared by employing the co-solvent with the derivatizing compound prior to the reaction between the derivatizing compound and the grafted polymer. After the derivatization reaction has been completed, the result will be a substantially improved flowable oil concentrate of the grafted and derivatized polymer.

EXAMPLE 25

A quantity of 34.5 grams of a maleic anhydride graft polymer (rubber) in which the polymer substrate comprised about 57 percent ethylene and 43 percent propylene having a number average molecular weight of about 30,200 on which has been grafted 3.4 weight percent of maleic anhydride in 103.5 grams of lubricant diluent oil was heated to 160° C. with mechanical stirring while the mixture was maintained under a nitrogen blanket. Once temperature was reached, mixing was continued for an additional hour at 160° C.

A quantity of 3.22 grams of neat 3-amino-N-(4-anilinophenyl)-butanamide was added to the oil solution of the polymer and a reaction effected over 4 hours at 160° C. under nitrogen. The Kinematic viscosity of the reaction mixture was then measured at 100° C. and found to be 11,000 cSt.

Dinonyl phenol (5.6 grams) was added as a co-solvent and the reaction mixture was stirred for an additional hour. The reaction mixture containing the derivatized graft polymer was then cooled and filtered. Again, the Kinematic Viscosity of the reaction product was measured at 100° C. and found to be 4200 cSt.

The invention has been described in detail with particular reference to preferred embodiments thereof, but it is understood that variations and modifications can be effected within the spirit and scope of the invention.

What is claimed is:

1. A composition of matter comprising an N-aromatic substituted acid amide compound selected from the group consisting of compounds of the formula:

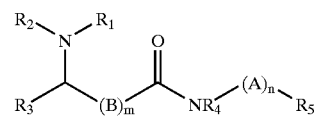

wherein

A and B are independently selected alkylene groups;

$R_1$ is selected from the group consisting of hydrogen, alkyl, alkylether, or ester;

$R_2$ is hydrogen if $R_1$ is hydrogen;

$R_2$ is an alkyl primary amine if $R_1$ is alkyl, alkylether, or ester;

$R_3$ and $R_4$ are independently selected from the group consisting of hydrogen and alkyl;

$R_5$ is a sterically hindered phenolic group,

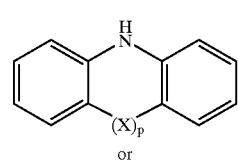

or

-continued

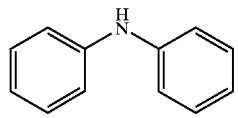

wherein

X is CH$_2$, S, NH, or O; and m, n, and p are independently selected integers equal to 0 or 1.

2. The composition of claim 1 wherein R$_5$ is

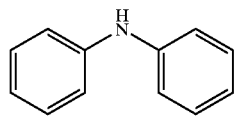

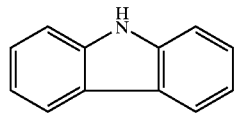

or

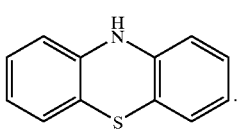

3. The composition of claim 1 wherein n is 0.

4. The composition of claim 1 wherein n is 1 and A is propylene.

5. The composition or claim 1 wherein R$_1$ and R$_2$ are both hydrogen.

6. The composition of claim 1 wherein R$_1$ is not hydrogen and R$_2$ is an alkyl primary amine.

7. The composition of claim 1 wherein m is 1 and B is methylene.

8. The composition of claim 1 wherein the N-aromatic substituted acid amide compound is 3-amino-N-(4-anilinophenyl)-butanamide, 3-amino-N-(4-anilinophenyl)-N-isopropyl butanamide, or N-(4-anilinophenyl)-3-{(3-aminopropyl)-(cocoalkyl)amino}butanamide.

9. A reaction product comprised of a carboxylic acid material bound to a substantially linear polymer, copolymer, or terpolymer, further reacted with an N-aromatic substituted acid amide moiety selected from the group consisting of compounds of the formula:

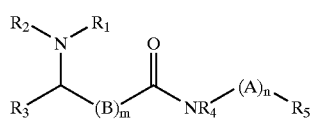

wherein

A and B are independently selected alkylene groups;

R$_1$ is selected from the group consisting of hydrogen, alkyl, alkylether, or ester;

R$_2$ is hydrogen if R$_1$ is hydrogen;

R$_2$ is an alkyl primary amine if R$_1$ is alkyl, alkylether, or ester;

R$_3$ and R$_4$ are independently selected from the group consisting of hydrogen and alkyl;

R$_5$ is a sterically hindered phenolic group,

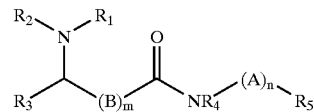

or

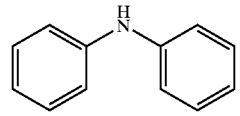

wherein

X is CH$_2$, S, NH, or O; and m, n, n, and p are independently selected integers equal to 0 or 1.

10. A lubricating oil composition comprising a major portion of lubricating oil and a minor portion of an additive that is an N-aromatic substituted acid amide compound or the reaction product comprised of a carboxylic acid material bound to a substantially linear polymer, copolymer, or terpolymer, further reacted with an N-aromatic substituted acid amide moiety, wherein said N-aromatic substituted acid amide is selected from the group consisting of compounds of the formula:

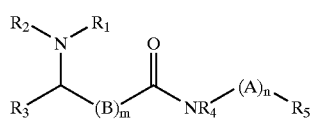

wherein

A and B are independently selected alkylene groups;

R$_1$ is selected from the group consisting of hydrogen, alkyl, alkylether, or ester;

R$_2$ is hydrogen if R$_1$ is hydrogen;

R$_2$ is an alkyl primary amine if R$_1$ is alkyl, alkylether, or ester;

R$_3$ and R$_4$ are independently selected from the group consisting of hydrogen and alkyl;

R$_5$ is a sterically hindered phenolic group,

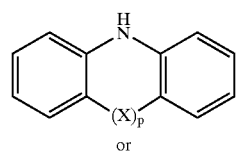

or

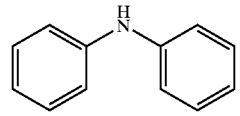

wherein

X is CH$_2$, S, NH, or O; and m, n, and p are independently selected integers equal to 0 or 1.

11. The lubricating oil composition of claim 10 further comprising a zinc dialkyldithiophosphate.

12. A composition of matter comprising a solution comprising:

(i) a reaction product comprised of a carboxylic acid material bound to a substantially linear polymer, copolymer, or terpolymer, further reacted with an N-aromatic substituted acid amide moiety selected from the group consisting of compounds of the formula:

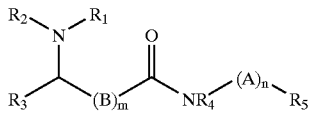

wherein

A and B are independently selected alkylene groups;

$R_1$ is selected from the group consisting or hydrogen, alkyl, alkylether, or ester;

$R_2$ is hydrogen if $R_1$ is hydrogen;

$R_2$ is an alkyl primary amine if $R_1$ is alkyl, alkylether, or ester;

$R_3$ and $R_4$ are independently selected from the group consisting of hydrogen and alkyl;

$R_5$ is a sterically hindered phenolic group,

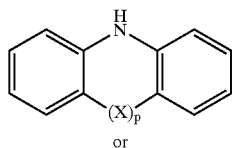

or

-continued

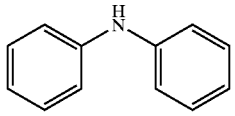

wherein

X is $CH_2$, S, NH, or O; and m, n, and p are independently selected integers equal to 0 or 1; and (ii) an oil solvent.

13. The composition of claim 12 wherein the oil solvent is mineral oil.

14. The composition of claim 12 further comprising a co-solvent.

15. The composition of claim 14 wherein the co-solvent is an alkyl, dialkyl, or mixed dialkyl phenol wherein each alkyl group is selected from the group consisting of alkyls is of from 6 to 22 carbon atoms.

16. A composition of matter comprising a solution comprising:

A) a reaction product comprised of a carboxylic acid material bound to a substantially linear polymer, copolymer, or terpolymer, further reacted with an N-alkyl imidazole;

B) an oil solvent; and

C) a co-solvent comprising an alkyl, dialkyl, or mixed dialkyl phenol, wherein the alkyl group is selected from the group consisting of alkyls of from 6 to 22 carbon atoms.

* * * * *